(12) United States Patent
Kastenhofer

(10) Patent No.: US 6,659,977 B2
(45) Date of Patent: *Dec. 9, 2003

(54) MULTILAYER INTERVENTIONAL CATHETER

(75) Inventor: Gerhard Kastenhofer, Zurich (CH)

(73) Assignee: Schneider (Europe) A.G., Bulach (CH)

( * ) Notice: Subject to any disclaimer, the term of this patent is extended or adjusted under 35 U.S.C. 154(b) by 24 days.

This patent is subject to a terminal disclaimer.

(21) Appl. No.: 09/978,964

(22) Filed: Oct. 15, 2001

(65) Prior Publication Data

US 2002/0022824 A1 Feb. 21, 2002

Related U.S. Application Data

(63) Continuation-in-part of application No. 09/317,293, filed on May 24, 1999, now Pat. No. 6,471,673, which is a continuation-in-part of application No. 08/936,352, filed on Sep. 24, 1997, now Pat. No. 5,961,765, and a continuation of application No. 08/845,569, filed on Apr. 25, 1997, now Pat. No. 6,319,228, which is a division of application No. 08/657,004, filed on May 28, 1996, now Pat. No. 6,843,032, which is a continuation of application No. 08/309,234, filed on Sep. 20, 1994, now abandoned.

(30) Foreign Application Priority Data

Oct. 27, 1993 (EP) .............................................. 93117403
Apr. 26, 1996 (EP) .............................................. 96106578

(51) Int. Cl.[7] .............................................. A61M 29/00
(52) U.S. Cl. ..................... 604/96.01; 604/264; 604/525
(58) Field of Search ........................ 604/96.01–103.14, 604/525, 264, 523, 524; 428/36.91; 606/192, 194; 138/140, 141, 145, 149, 146, 118; 156/242, 293, 244.11, 244.12, 294

(56) References Cited

U.S. PATENT DOCUMENTS

| | | |
|---|---|---|
| 3,561,493 A | 2/1971 | Maillard |
| 3,618,614 A | 11/1971 | Flynn |
| 3,695,921 A | 10/1972 | Sheperd et al. |
| 3,814,137 A | 6/1974 | Martinez |
| 3,890,976 A | 6/1975 | Bazell et al. |
| 4,157,932 A | 6/1979 | Hirata |
| 4,171,416 A | 10/1979 | Motegi et al. |
| 4,211,741 A | 7/1980 | Ostoich |
| 4,265,848 A | 5/1981 | Rusch |
| 4,282,876 A | 8/1981 | Flynn |

(List continued on next page.)

FOREIGN PATENT DOCUMENTS

| | | |
|---|---|---|
| CA | 2078201 A1 | 12/1992 |
| EP | 0 277 368 A1 | 8/1988 |
| EP | 0 279 959 B1 | 8/1988 |
| EP | 0 298 634 A1 | 1/1989 |
| EP | 0 351 687 A2 | 1/1990 |
| EP | 0 358 117 B1 | 3/1990 |

(List continued on next page.)

OTHER PUBLICATIONS

"Abrasion & Wear," Encyclopedia of Polymer Science and Engineering, vol. 1, A to Amorphous Polymers, A Wiley–Interscience Publication (1985) pp. 1–35.
"Asuka™ 2.9F OTW PTCA Balloon Catheter," Feb. 1994.
"Physical Constants of Important Polymers," Polymer Handbook, 2nd Edition, A Wiley–Interscience Publication (1975) pp. V–13 thru V–22.
"Physical Constants of Poly(Vinyl Chloride)," Polymer Handbook, 2nd Edition, A Wiley–Interscience Publication (1975) pp. V–41 thru V–50.
Bynel® Coextrudable Adhesive Resins Selector Guide (6 Sheets).

(List continued on next page.)

*Primary Examiner*—Brian L. Casler
*Assistant Examiner*—Cris L. Rodriguez
(74) *Attorney, Agent, or Firm*—Crompton, Seager & Tufte, LLC

(57) ABSTRACT

The catheter comprises a catheter tube formed of two superposed tubular layers of materials which differ from one another. A tubular mediator layer is arranged between the layers to provide an adhesive anchorage for the layers.

10 Claims, 3 Drawing Sheets

U.S. PATENT DOCUMENTS

| | | |
|---|---|---|
| 4,323,071 A | 4/1982 | Simpson et al. |
| 4,335,723 A | 6/1982 | Patel |
| 4,413,989 A | 11/1983 | Schjeldahl et al. |
| 4,596,563 A | 6/1986 | Pande |
| 4,597,755 A | 7/1986 | Samson et al. |
| 4,627,844 A | 12/1986 | Schmitt |
| 4,636,346 A | 1/1987 | Gold et al. |
| 4,646,719 A | 3/1987 | Neuman et al. |
| 4,702,252 A | 10/1987 | Brooks et al. |
| 4,707,389 A | 11/1987 | Ward |
| 4,729,914 A | 3/1988 | Kliment et al. |
| 4,744,366 A | 5/1988 | Jang |
| 4,762,129 A | 8/1988 | Bonzel |
| 4,762,129 A | 8/1988 | Bonzel |
| 4,763,654 A | 8/1988 | Jang |
| 4,769,099 A | 9/1988 | Therriault et al. |
| 4,775,371 A | 10/1988 | Mueller, Jr. |
| 4,776,849 A | 10/1988 | Shinno et al. |
| 4,782,834 A | 11/1988 | Maguire et al. |
| 4,820,349 A | 4/1989 | Saab |
| 4,863,449 A | 9/1989 | Therriault et al. |
| 4,900,314 A | 2/1990 | Quackenbush |
| 4,906,244 A | 3/1990 | Pinchuk et al. |
| 4,921,483 A | 5/1990 | Wijay et al. |
| 4,923,450 A | 5/1990 | Maeda et al. |
| 4,940,179 A | 7/1990 | Soni |
| 4,955,895 A | 9/1990 | Sugiyama et al. |
| 4,960,410 A | 10/1990 | Pinchuk |
| 4,976,690 A | 12/1990 | Solar et al. |
| 4,976,720 A | 12/1990 | Machold et al. |
| 4,981,478 A | 1/1991 | Evard et al. |
| 4,994,018 A | 2/1991 | Saper |
| 4,994,032 A | 2/1991 | Sugiyama et al. |
| 4,994,047 A | 2/1991 | Walker et al. |
| 5,006,119 A | 4/1991 | Acker et al. |
| 5,026,377 A | 6/1991 | Burton et al. |
| 5,035,694 A | 7/1991 | Kasprzyk et al. |
| 5,041,089 A | 8/1991 | Mueller et al. |
| 5,041,100 A | 8/1991 | Rowland et al. |
| 5,047,045 A | 9/1991 | Arney et al. |
| 5,059,269 A | 10/1991 | Hu et al. |
| 5,063,018 A | 11/1991 | Fontirroche et al. |
| 5,078,727 A | 1/1992 | Hannam et al. |
| 5,085,649 A | 2/1992 | Flynn |
| 5,100,381 A | 3/1992 | Burns |
| 5,100,386 A | 3/1992 | Inoue |
| 5,114,423 A | 5/1992 | Kasprzyk et al. |
| 5,120,323 A | 6/1992 | Shockey et al. |
| 5,147,315 A | 9/1992 | Weber |
| 5,195,969 A | 3/1993 | Wang et al. |
| 5,195,971 A | 3/1993 | Sirhan |
| 5,221,270 A | 6/1993 | Parker |
| 5,234,416 A | 8/1993 | Macaulay et al. |
| 5,250,069 A | 10/1993 | Nobuyoshi et al. |
| 5,254,090 A | 10/1993 | Lombardi et al. |
| 5,267,959 A | 12/1993 | Forman |
| 5,270,086 A | 12/1993 | Hamlin |
| 5,272,012 A | 12/1993 | Opolski |
| 5,279,560 A | 1/1994 | Morrill et al. |
| 5,290,230 A | 3/1994 | Ainsworth et al. |
| 5,290,306 A | 3/1994 | Trotta et al. |
| 5,304,134 A | 4/1994 | Kraus et al. |
| 5,338,299 A | 8/1994 | Barlow |
| 5,348,536 A | 9/1994 | Young et al. |
| 5,356,709 A | 10/1994 | Woo et al. |
| 5,383,853 A | 1/1995 | Jung et al. |
| 5,397,306 A | 3/1995 | Nobuyoshi et al. |
| 5,403,292 A | 4/1995 | Ju |
| 5,405,338 A | 4/1995 | Kranys |
| 5,409,495 A | 4/1995 | Osborn |
| 5,423,754 A | 6/1995 | Cornelius et al. |
| 5,425,712 A | 6/1995 | Goodin |
| 5,439,454 A | 8/1995 | Lo et al. |
| 5,460,608 A | 10/1995 | Lodin et al. |
| 5,478,320 A | 12/1995 | Trotta |
| 5,484,444 A | 1/1996 | Braunschweiler et al. |
| 5,499,973 A | 3/1996 | Saab |
| 5,501,759 A | 3/1996 | Forman |
| 5,514,236 A | 5/1996 | Avellanet et al. |
| 5,527,281 A | 6/1996 | Haas |
| 5,533,985 A | 7/1996 | Wang |
| 5,538,510 A | 7/1996 | Fontirroche et al. |
| 5,545,151 A | 8/1996 | O'Connor et al. |
| 5,549,552 A | 8/1996 | Peters et al. |
| 5,558,737 A | 9/1996 | Brown et al. |
| 5,562,127 A | 10/1996 | Fanselow et al. |
| 5,571,089 A | 11/1996 | Crocker |
| 5,620,649 A | 4/1997 | Trotta |
| 5,643,209 A | 7/1997 | Fugoso et al. |
| 5,653,691 A | 8/1997 | Rupp et al. |
| 5,676,659 A | 10/1997 | McGurk |
| 5,728,063 A | 3/1998 | Preissman et al. |
| 5,728,088 A | 3/1998 | Magruder et al. |
| 5,733,400 A | 3/1998 | Gore et al. |
| 5,749,852 A | 5/1998 | Schwab et al. |
| 5,792,814 A | 8/1998 | Oishi et al. |
| 5,797,877 A | 8/1998 | Hamilton et al. |
| 5,820,594 A | 10/1998 | Fontirroche et al. |
| 5,824,173 A | 10/1998 | Fontirroche et al. |
| 5,837,313 A | 11/1998 | Ding et al. |
| 5,843,032 A | 12/1998 | Kastenhofer |
| 5,853,400 A | 12/1998 | Samson |
| 5,961,765 A | 10/1999 | Kastenhofer |
| 6,027,477 A | 2/2000 | Kastenhofer |
| 6,165,166 A | 12/2000 | Samuelson et al. |
| 6,319,228 B1 | 11/2001 | Kastenhofer |
| 6,471,673 B1 * | 10/2002 | Kastenhofer ........... 604/103.06 |

FOREIGN PATENT DOCUMENTS

| | | |
|---|---|---|
| EP | 0 380 102 A1 | 8/1990 |
| EP | 0 420 488 A1 | 4/1991 |
| EP | 0 436 501 B1 | 7/1991 |
| EP | 0 452 123 A1 | 10/1991 |
| EP | 0 456 342 A1 | 11/1991 |
| EP | 0 520 692 A1 | 12/1992 |
| EP | 0 530 201 B1 | 3/1993 |
| EP | 0 650 740 A1 | 5/1995 |
| EP | 0 669 142 A2 | 8/1995 |
| EP | 0 803 264 A1 | 10/1997 |
| GB | 2 130 093 A | 5/1984 |
| GB | 2 209 121 A | 5/1989 |
| WO | WO 89/02763 A1 | 4/1989 |
| WO | WO 92/11893 A1 | 7/1992 |
| WO | WO 93/05842 A1 | 4/1993 |
| WO | WO 95/18647 A2 | 7/1995 |

OTHER PUBLICATIONS

Chevron Chemical Company Technical Data Sheet Ethylene–Methyl Acrylate Copolymer EMAC SP 2260 (2 Sheets).

Chevron Chemical Company Technical Data Sheet Ethylene–Methyl Acrylate Copolymer EMAC 2205 (2 Sheets).

DSM Engineering Plastics Arnitel®—Available Grade List (4 Sheets).

DuPont Hytrel® Polyester Elastomer Hytrel 7246 (2 Sheets).

Gaylord, Norman G. et al., "Compatibilizing Agents: Structure and Function in Polyblends," *J. Macromol. Sci–Chem.*, A26(8) (1989) pp. 1211–1229.

Gaylord, Norman G., "Maleation of Linear Low–Density Polyethylene by Reactive Processing," *Journal of Applied Polymer Science*, vol. 44, No. 11, Apr. 15, 1992, pp. 1941–1949.

Opti–Plast PTA Balloon Dilatation Catheters: for Peripheral Angioplasty (4 Sheets).

Petrothene® LM 6007–00 (1 Sheet.

Petrothene® LS 5060–00 (1 Sheet).

Plexar® PX 209 (2 Sheets).

Plexar® PX 360 (2 Sheets).

Plexar® Tie–Layer Resigns, Products, Applications, and Key Properties (3 Sheets).

Quantum Chemical Corporation Material Safety Data Sheet Plexar® (5 Sheets).

* cited by examiner

MULTILAYER INTERVENTIONAL CATHETER

This application is continuation of U.S. patent application Ser. No. 08/845,569, filed Apr. 25, 1997, now U.S. Pat. No. 6,319,228 which claims priority to European Patent Application No. 96106578.6, filed Apr. 26, 1996. This application is also a continuation-in-part of U.S. patent application Ser. No. 09/317,293, filed May 24, 1999, now U.S. Pat. No. 6,471,673 which is a continuation of U.S. patent application Ser. No. 08/936,352, filed Sep. 24, 1997, now U.S. Pat. No. 5,961,765 which is a divisional of U.S. patent application Ser. No. 08/657,004, filed on May 28, 1996, now U.S. Pat. No. 5,843,032, which is a continuation of U.S. patent application Ser. No. 08/309,234, filed on Sep. 20, 1994, now abandoned, which claims priority to European Patent Application No. 93117403.1, filed Oct. 27, 1993, the entire disclosures of which are hereby incorporated by reference.

BACKGROUND OF THE INVENTION

This invention relates to an interventional catheter comprising a catheter tube having two superposed layers of materials secured together and with mechanical properties differing from one another, a guidewire lumen in the catheter tube for the sliding fit of a guidewire, and a balloon with a distal end sealingly surrounding the catheter tube whereby the catheter tube has an inner layer forming the guidewire lumen and an outer layer forming an outer surface of the catheter tube.

Over the wire catheters have been widely used for interventions such as percutaneous transluminal cardiovascular angioplasty. A problem with these catheters is that the guidewire may clog into the guidewire lumen of the catheter, whereby the guidewire may follow the balloon upon withdrawal thereof after the inflation procedure thereby making it necessary to re-insert the guidewire into the treated area of the blood vessel for repositioning a balloon therein in case a second inflation is needed. A further problem is that the catheter has to achieve an acceptable compromise between the requirements of some stiffness to assure good pushability and some flexibility to assure kink resistance. In addition, the catheter has to permit safe attachment of the balloon to the catheter tube.

Monorail® technology, which provides for an entry of the guidewire distal of the balloon and an exit for the guidewire distal of the proximal end of the catheter tube, substantially reduces the risk of the guidewire clogging in the guidewire lumen because the length of frictional engagement between the guidewire and the guidewire lumen is strongly reduced. That is also of great help in the handling of balloon catheters for balloon exchange purposes. Though limited, the friction and clogging problem is, however, still existent.

Two layer catheter shafts have been developed. For example, the document WO 92/11893 describes an intraaortic balloon apparatus comprising a hollow catheter in which is located an elongated member forming a central lumen extending out of the catheter at the distal end thereof. An aortic pumping balloon is positioned over the elongated member; the distal end of the balloon is bonded to a tip affixed to the distal end of the elongated member, and its proximal end is bonded to the distal end of the catheter. In order to achieve a balance of flexibility and remains and to avoid kinking, the elongated member is formed of an inner layer comprised of a soft elastomeric material to impart flexibility to the tubing and the outer layer is comprised of a hard plastic material to impart structural support to the elongated member. This balloon apparatus cannot be loaded with a guidewire and moved into tortuous vessels with the guidewire loaded inside the elongated member as the friction between guidewire and elongated member increases distinctively when the elongated member is shaped into curves. There would be therefore the risk that a spiral wound guidewire could be captured in the soft elastomeric plastic material of the inner layer of the elongated member. Although the outer layer of the elongated member that is coextruded onto the inner layer is formed of nylon, a material which is expected to be directly weldable to a wide variety of materials, this balloon apparatus cannot be introduced into narrow vessels or narrow stenoses, nor can it be passed through narrow punctures to enter the blood vessels. This is because of the relatively large profile of the folded balloon, due to the distal fixture of the balloon to the elongated member. The balloon is bonded to an intermediate tip element which in turn is bonded to the elongated member.

The document EP 0 650 740 A1 shows a catheter comprising a catheter tube having two superposed layers of materials secured in relation to one another and with mechanical properties differing from one another, a longitudinal lumen in the catheter tube for the sliding fit of a guidewire, and a balloon with a proximal end and a distal end, the distal end sealingly surrounding the catheter tube, whereby the catheter tube has an inner layer forming the longitudinal lumen and an outer layer forming the outer surface of the catheter tube. In this catheter, the inner layer is formed of a material with lower friction coefficient than the material forming the outer layer, whereby there is no more risk of having the guidewire clogging in the guidewire lumen of the catheter tube.

In terms of two layers catheter shafts, it has been observed that in practical use the adhesion of the two layers of material was not absolutely satisfactory. Although the coextrusion technology currently used for making such catheter shafts seems to involve close molecular interpenetration of the materials forming the superposed layers of the shaft, it has been possible to observe separation of the two layers, for example at the place of insertion of the shaft over the guidewire. Furthermore, tear test effected on such structures has shown that the two layers can separate under extreme conditions of stress on the shaft.

It is an object of this invention to propose an interventional balloon catheter avoiding the aforesaid drawbacks A further object of the invention is an interventional catheter structure which is versatile and which provides a fully controllable and easy to manufacture assembly. Still a further object of the invention is an interventional low profile balloon catheter that can be safely operated on a guidewire and moved into tortuous vessels and other extreme conditions.

Various multilayer catheters are known in the art. Reference is made to U.S. Pat. Nos. 4,627,844; 4,636,346; 5,403,292; 5,499,973; and 5,538,510.

All documents cited herein, including the foregoing, are incorporated herein by reference in their entireties for all purposes.

SUMMARY OF THE INVENTION

Accordingly, where the catheter comprises mediator layer means arranged between the inner layer and the outer layer for the adhesive anchorage of the layers thereto, securing of the inner layer and outer layer is strongly enhanced independently of their intrinsic capacity of adhesion to one another. The risk of a poor adhesion or the risk of a failure in the adhesion of the two layers to one another is eliminated. The inner and outer layers may be chosen for their most appropriate mechanical characteristics rather than for their capacity to adhere to one another. Because of the adhesive anchorage of the inner and outer layers on the mediator layer means, the risk of separation of the two layers upon insertion of the catheter tube over a guidewire is minimized. And the assembly of inner and outer layers is under control and the possibilities of changing the flexibility of the assembly are improved; due to the adhesive anchorage on the mediator layer means, rigidity of the assembly is enhanced with the same basic inner and outer layers, whereas flexibility of the assembly may be mastered by safely acting on the thickness of the inner and outer layers, with the resulting reduction in the profile of the catheter. As a result of the adhesive anchorage of the inner and outer layers on the mediator layer means the assembly behaves like a unit; accordingly, the assembly may be safely grabbed by the outer layer and tear tests are thus facilitated.

The inner and outer layers and the mediator layer means may be congruent in length, so that the catheter shaft can be produced in long tubes which may be cut at will to the appropriate length. Where the inner layer, the mediator layer means and the outer layer are coextruded, a catheter tube is formed in a continuous process avoiding the need of using a core in the inner layer.

Where the inner and outer layers are substantially transparent and the mediator layer means are contrasted with respect to the substantially transparent inner and outer layers, a visual control of the assembly is readily available to further improve the manufacture.

Where the mediator layer means have mechanical properties differing from the mechanical properties of the inner and outer layers a further step is achieved in the possibility of changing the lengthwise flexibility properties of the catheter.

When the inner layer is formed of a material with lower friction coefficient than the material forming the outer layer, there is no more risk of having the guidewire clogging or being captured in the guidewire lumen of the catheter tube. Withdrawal and re-positioning of the balloon catheter on a guidewire left in place at the site of treatment in the vessel system is rapid, safe and precise. Furthermore, the choice can be made for materials for the inner and outer layers having the most appropriate friction and kink resistance coefficients, while safe attachment of the balloon may be made at will on the outer layer which is chosen without being influenced by the friction properties of the inner layer.

The mediator layer means may be formed on the basis of a low density polyethylene to offer superior adhesion performance in a wide variety of configurations of the inner and outer layers and ease of processing on conventional fabrication equipment.

In a preferred form of the invention, the inner layer is made of a polyethylene or of a high density polyethylene, both of which assure an extremely low friction coefficient and an appropriate kink resistance coefficient. In another preferred form of the invention, the outer layer is made of a polyamid to assure easy welding of the balloon and a good stiffness at that level.

In sum, the invention relates to an interventional catheter comprising a catheter tube having two superposed layers of materials secured together and with mechanical properties differing from one another. A guidewire lumen is formed in the catheter tube for the sliding fit of a guidewire, and a balloon with a distal end sealingly surrounding the catheter tube. The catheter tube has an inner layer forming the guidewire lumen and an outer layer forming an outer surface of the catheter tube wherein it comprises mediator layer means arranged between the inner layer and the outer layer for the adhesive anchorage of the layers thereto. The inner and outer layers and the mediator layer means may be congruent in length. The inner layer, the mediator layer means, and the outer layer may be coextruded. The inner and outer layers may be substantially transparent and the mediator layer means may be contrasted with respect to the substantially transparent inner and outer layers. The mediator layer means may have mechanical properties differing from mechanical properties of the inner and outer layers. The inner layer may be formed of a material with lower friction coefficient than the material forming the outer layer. The mediator layer means may be formed on the basis of a low density polyethylene. The inner layer may be made of a polyethylene. The inner layer may be made of a high density polyethylene. The outer layer may be made of a polyamid.

These and other objects, features and advantages of the invention will become readily apparent from the following description with reference to the accompanying drawings which show, diagrammatically and by way of example only, preferred but still illustrative embodiments of the invention.

As will be realized, the invention is capable of other and different embodiments and methods of construction, and its several details are capable of modification in various obvious respects, all without departing from the invention. Accordingly, the drawing and description are to be regarded as illustrative in nature, and not as restrictive.

DETAILED DESCRIPTION OF THE INVENTION

Figure 1:
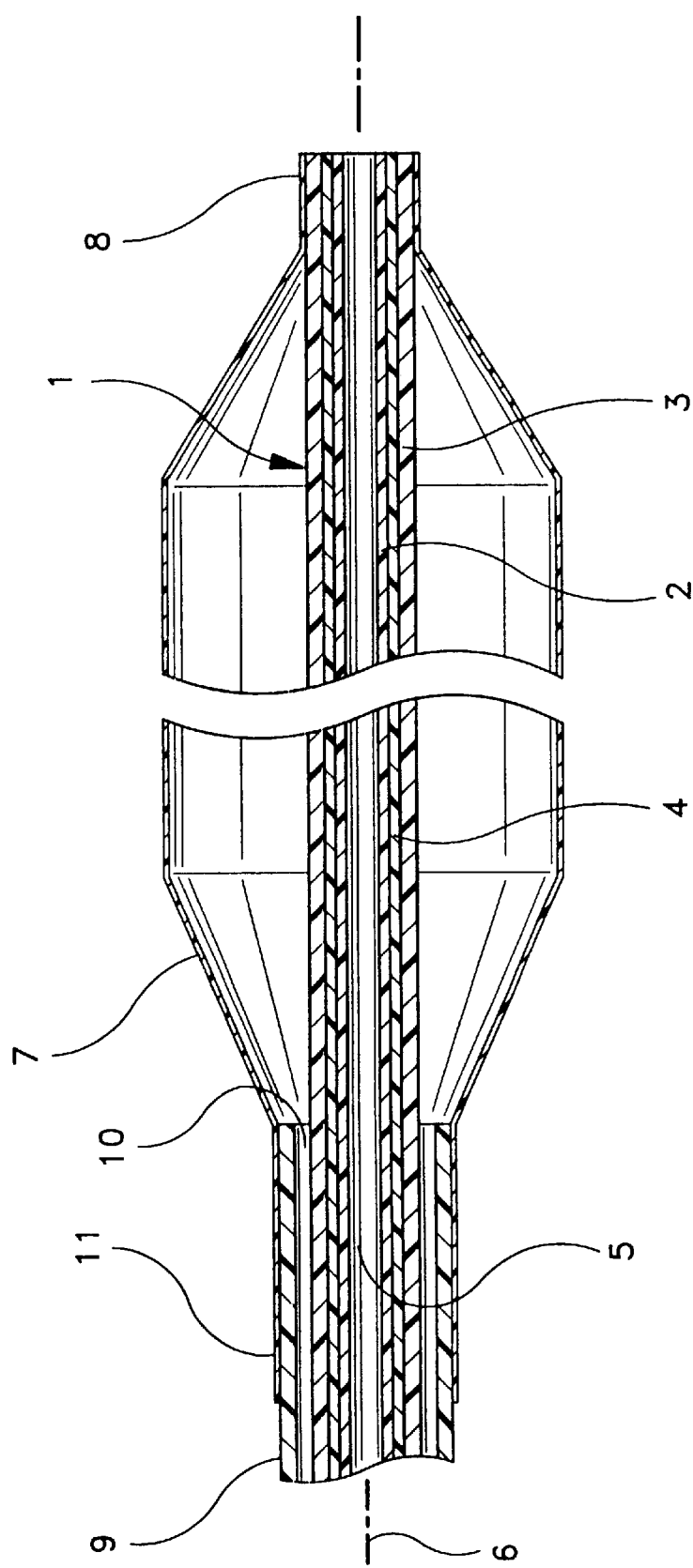
FIG. 1 is a longitudinal cross-sectional view of an over the wire balloon catheter embodying the invention.

The interventional catheter shown in FIG. 1 comprises a catheter tube 1 formed of two superposed tubular layers of materials 2 and 3 with a tubular mediator layer 4 arranged therebetween for the adhesive anchorage of the layers 2 and 3 onto the mediator layer 4.

The tubular layers 2, 3 and 4 extend all over the length of catheter tube 1, being thus congruent in length, and the assembly of layers forming the catheter tube 1 may be obtained by the known coextrusion technology, i.e., by extruding simultaneously the inner layer 2 with the mediator layer 4 and with the outer layer 3 thereover. Layers 2 and 3 have mechanical properties differing from one another and, preferably, mediator layer 4 also has mechanical properties differing from the mechanical properties of inner and outer layers 2 and 3.

Preferably, the inner layer 2 is formed of a material with lower friction coefficient than the material forming the outer layer 3. For example, the inner layer 2 may be formed of a polyethylene, preferably a high density polyethylene, whereas the outer layer 3 may be formed of a polyamid. The mediator layer 4 may be formed on the basis of a low density polyethylene.

Preferably, the inner and outer layers 2 and 3 are substantially transparent, whereas the mediator layer 4 is contrasted with respect to the substantially transparent inner and outer layers 2 and 3.

The catheter tube 1 has thus a longitudinal lumen 5 for the sliding fit of a guidewire exemplified by dotted line 6, which lumen 5 has a very low friction coefficient, lower than that of the outer layer 3, and a non-kinking capacity while the outer layer 3 forms an outer surface of the catheter tube 1 and is easily weldable to the materials commonly used for making balloons for angioplasty purposes and the like. And therebetween, the mediator layer 4 assures the best adhesive anchorage of inner and outer layers 2 and 3 thereto, the catheter tube 1 thus behaving as a unitary element with differentiating properties at its inner and outer levels.

Over the distal portion of the catheter tube 1 is positioned a balloon 7 the distal end 8 of which sealingly surrounds the outer layer 3 of catheter tube 1, for example by welding.

A tube 9 is arranged over the catheter tube 1, at a radial distance thereof, thus defining an inflation lumen 10 for the balloon 7. The proximal end 11 of the balloon 7 is welded onto the distal end of tube 9.

Figure 2:
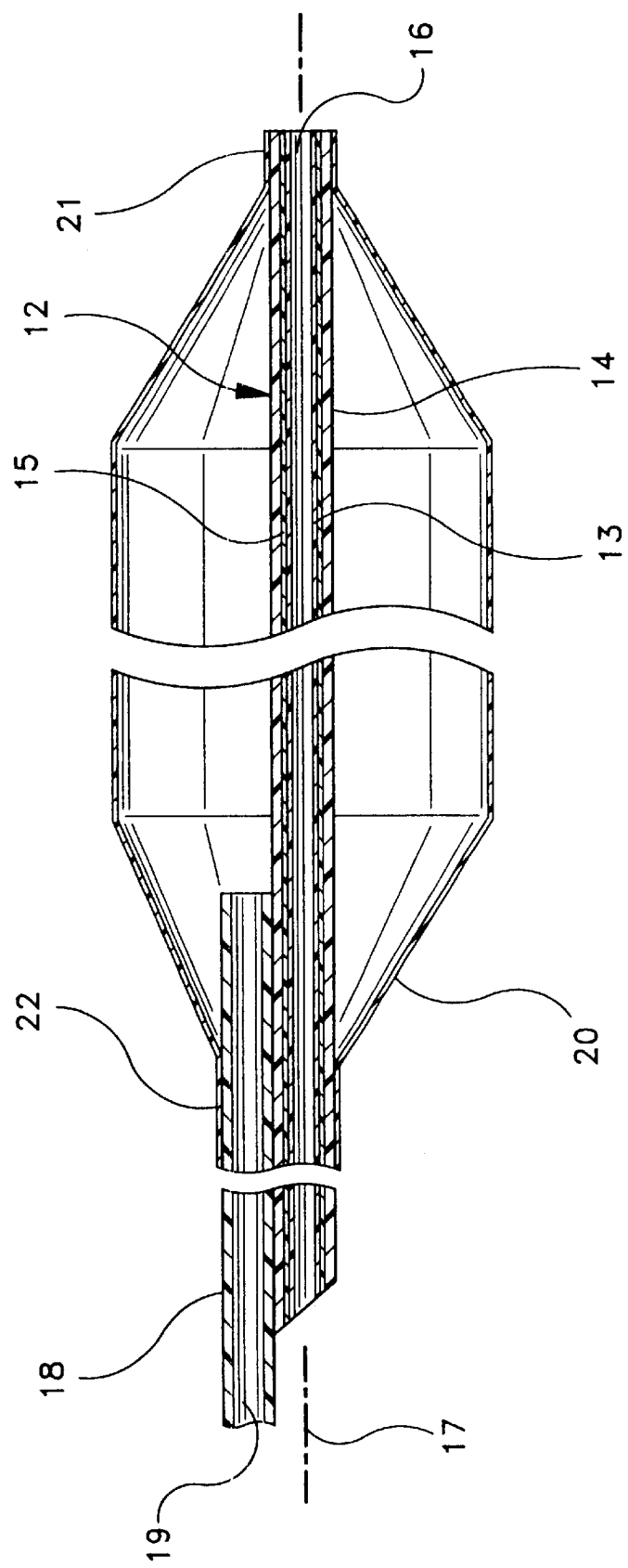
FIG. 2 is a longitudinal cross-sectional view of a Monorail® balloon catheter embodying the invention.

The interventional catheter shown in FIG. 2 also comprises a catheter tube 12 having two superposed tubular layers of materials 13 and 14 with a tubular mediator layer 15 arranged therebetween for adhesive anchorage of the layers 13 and 14 onto the mediator layer 15.

The tubular layers 13, 14 and 15 extend all over the catheter tube 12 and the assembly of layers forming the catheter tube 12 may also be obtained by the known coextrusion technology whereby inner tubular layer 13 is extruded simultaneously with the mediator layer 15 and the outer layer 14 thereover. Layers 13 and 14 have mechanical properties differing from one another and, preferably, mediator layer 15 also has mechanical properties differing from the mechanical properties of inner and outer layers 13 and 14.

Preferably the inner layer 13 is made of a material with lower friction coefficient than the material forming the outer layer 14. For example, inner layer 13 may be formed of a polyethylene, preferably a high density polyethylene, whereas the outer layer 14 may be made of a polyamid. The mediator layer 15 may be formed on the basis of a low density polyethylene.

Preferably the inner and outer layers 13 and 14 are substantially transparent and the mediator layer 15 is contrasted with respect to the substantially transparent inner and outer layers 13 and 14.

The catheter tube 12 has thus a longitudinal lumen 16 for the sliding fit of a guidewire exemplified by dotted line 17, which lumen 16 has a very low friction coefficient, lower than that of the outer layer 14 and with a non-kinking capacity, whereas outer layer 14 forms an outer surface of the catheter tube 12 and is easily weldable to the materials currently used for making angioplasty balloons. And therebetween, the mediator layer 15 also assures superior adhesive anchorage for inner and outer layers 13 and 14, the catheter tube 12 acting as a unit with different properties at its inner and outer levels.

A tube 18 is affixed, for example welded, in parallel relationship to the proximal portion of catheter tube 12, and this tube 18 extends proximally of the catheter tube 12. The tube 18 defines an inflation lumen 19 for a balloon 20 the distal end 21 of which sealingly surrounds the outer layer 14 of catheter tube 12, for example by welding. The proximal end 22 of balloon 20 sealingly surrounds a proximal portion of the catheter tube 12 and a distal portion of tube 18, whereby the proximal portion of catheter tube 12 extends proximally out of the balloon 20 and the distal portion of tube 18 extends within the balloon 20.

Variants are readily available. For example, the mediator layer may be made of two superposed tubular layers of materials which differ from one another in order to respectively provide superior adhesive anchorage for the inner and outer layers while assuring total adhesive anchorage between them. This configuration is advantageous for example to match particular flexibility requirements for the catheter tube or to assume adhesive anchorage conditions which would be otherwise difficult for the inner and outer layers.

Figure 3:
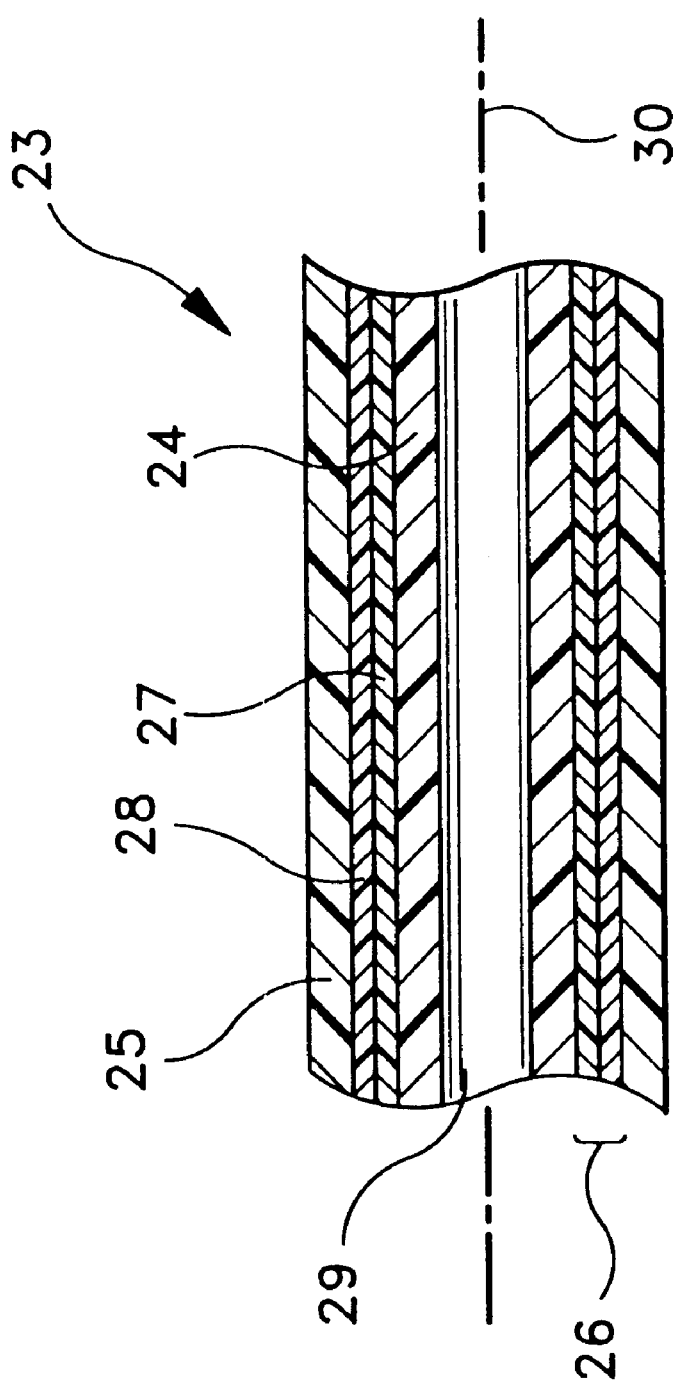
FIG. 3 is an enlarged cross-sectional view of a variant catheter embodiment of the invention.

FIG. 3 shows such a configuration where the catheter tube 23 is formed of two superposed tubular layers of materials 24 and 25 with a tubular mediator layer 26 arranged therebetween and formed of two superposed adhesively anchored tubular layers 27 and 28, layer 27 being for adhesive anchorage of inner layer 24 and layer 28 for adhesive anchorage of outer layer 25. Within inner layer 24 is the guidewire lumen 29 for the sliding fit of a guidewire exemplified by dotted line 30.

It will be evident from considerations of the foregoing that the Multilayer Interventional Catheter is now available, and may be constructed using a number of methods and materials, in a wide variety of sizes and styles for the greater efficiency and convenience of a user.

The above described embodiments of the invention are merely descriptive of its principles and are not to be considered limiting. Further modifications of the invention herein disclosed will occur to those skilled in the respective arts and all such modifications are deemed to be within the scope of the invention as defined by the following claims.

What is claimed is:

1. A catheter comprising: a first catheter tube having at least two superposed layers of materials, including an inner layer and an outer layer, with a low-density polyethylene mediator layer arranged between the inner layer and outer layer, secured together and with mechanical properties differing from one another, a lumen in the first catheter tube, and a balloon sealingly surrounding the first catheter tube, whereby the inner layer comprises high-density polyethylene and forms the lumen, and the outer layer comprises a polymer and forms an outer surface of the first catheter tube.

2. A catheter as in claim 1, wherein the outer layer comprises polyamide.

3. A catheter as in claim 1, further comprising: a second catheter tube disposed about the first catheter tube.

4. A catheter as in claim 3, wherein a proximal end of the balloon is connected to a distal end of the second tube, and a distal end of the balloon is connected to a distal end of a first tube.

5. A catheter comprising: a catheter tube having at least two superposed layers of materials, including an inner layer and an outer layer, secured together and with mechanical properties differing from one another, a guidewire lumen in the catheter tube for the sliding fit of a guidewire, and a balloon with a distal end sealingly surrounding the catheter tube, wherein the inner layer comprises high-density polyethylene and forms the guidewire lumen, and the outer layer comprises a polymer and forms an outer surface of the catheter tube, and wherein the catheter tube further comprises a mediator layer of low-density polyethylene arranged between the inner layer and the outer layer.

6. A catheter comprising:
(a) a tube comprising:
  (i) an outermost layer comprising a polymer having a first coefficient of friction;
  (ii) an innermost layer coextensive with the outermost layer and forming a lumen, the innermost layer comprising a high-density polyethylene having a second coefficient of friction which is less than the first coefficient of friction; and
  (iii) a middle layer disposed between the outermost layer and the innermost layer and affixing the outermost layer to the innermost layer, the middle layer comprising a low-density polyethylene; and
(b) a balloon sealed to the tube.

7. A catheter comprising:
(a) a first tube comprising:
  (i) an outermost layer comprising a polymer having a first coefficient of friction;
  (ii) an innermost layer coextensive with the outermost layer and forming a lumen, the innermost layer comprising a high-density polyethylene having a second coefficient of friction which is less than the first coefficient of friction; and
  (iii) a middle layer disposed between the outermost layer and the innermost layer and affixing the outermost layer to the innermost layer, the middle layer comprising a low-density polyethylene;
(b) a second tube disposed about a portion of the first tube; and
(c) a balloon with a distal end sealingly surrounding the first tube and a proximal end sealingly surrounding the second tube.

8. A balloon catheter, comprising:
a first elongate catheter tube having a proximal end, a distal end and a lumen extending therethrough, the first tube including an inner layer, an intermediate layer disposed on the inner layer, and an outer layer disposed on the intermediate layer, the inner layer comprising a high density polyethylene polymer, the intermediate layer comprising a low density polyethylene polymer, and the outer layer comprising a polymer with mechanical properties differing from that of the inner layer; and
a balloon connected to the distal end of the first tube.

9. A balloon catheter as in claim 8, further comprising: a second elongate catheter tube disposed about the first catheter tube.

10. A balloon catheter as in claim 9, wherein a proximal end of the balloon is connected to a distal end of the second tube, and a distal end of the balloon is connected to the distal end of the first tube.

* * * * *